United States Patent [19]

Yu et al.

[11] 4,328,245

[45] May 4, 1982

[54] CARBONATE DIESTER SOLUTIONS OF PGE-TYPE COMPOUNDS

[75] Inventors: Cheng-Der Yu, Mountain View; Ursula Bruenner, Palo Alto, both of Calif.

[73] Assignee: Syntex (U.S.A.) Inc., Palo Alto, Calif.

[21] Appl. No.: 234,240

[22] Filed: Feb. 13, 1981

[51] Int. Cl.$^3$ .................. A61K 31/215; A61K 31/19
[52] U.S. Cl. .................................... 424/305; 424/317
[58] Field of Search .............................. 424/305, 317

[56] References Cited

PUBLICATIONS

Kurono et al., Chem. Abst., vol. 91, (1979), p. 78903v.

Primary Examiner—Sam Rosen
Attorney, Agent, or Firm—James M. Kanagy; Alan M. Krubiner; Tom M. Moran

[57] ABSTRACT

Stable compositions of PGE-type compounds are achieved by dissolving those compounds in carbonate diester solvents which may contain water up to the solubility limit of the carbonate diester.

10 Claims, No Drawings

CARBONATE DIESTER SOLUTIONS OF PGE-TYPE COMPOUNDS

BACKGROUND OF THE INVENTION

1. Field of the Invention

This invention relates to novel compositions of PGE-type prostaglandins; a method for stabilizing PGE-type compounds in solution; and to a process for dispensing PGE-type prostaglandins for oral adminstration.

2. Related Disclosures

Prostaglandins have classically been described as chemically related 20 carbon chain hydroxy fatty acids having the basic skeleton of prostanoic acid:

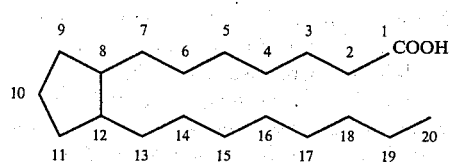

this structure is the basis for prostaglandin numbering and nomenclature.

Naturally occuring prostaglandins are derivatives of prostanoic acid. For descriptive purposes, four types are recognized. The type distinction is based primarily on pentane ring subtituents and structural orientation. Although they can be named as derivatives of prostanoic acid, they are conventionally referred to by the letters A, B, E and F. Prostaglandins having an hydroxyl group at the C-11 position and a keto group at the C-9 position are known as PGE or PGE-type compounds. Those having hydroxyl groups at C-9 and C-11 are known as the PGF series and are further designated by an α or β suffix to indicate the configuration of the hydroxyl group at said position. Series A and B have a keto group at C-9 and a double bond between C-10 and C-11 or C-8 and C-12 respectively. The natural compounds are the α-hydroxy substituted compounds. Prostaglandins may contain different series of unsaturation in the molecule, particularly at C-5, C-13 and C-17. The unsaturation is also indicated by a suffix. Thus, for example, $PGF_1$ and $PGE_1$ series refer to prostanoic acids having a trans-olefin bond at the C-13 position, while the $PGF_2$ and $PGE_2$ series refer to prostadienoic acids having a cis-olefin bond at the C-5 position and a trans-olefin bond at the C-13 position. For a review on prostaglandins and the definition of primary prostaglandins, see for example, S. Bergstrom, Recent Progress in Hormone Research 22, pp. 153–175 (1966) and Science 157, p. 382 (1967) by the same author.

Prostagladins generally act to stimulate gastrointestional and reproductive smooth muscles, affect relaxation and contraction of respiratory smooth muscle, are hypotensives, and inhibit lipolysis of fatty acids, gastric acid secretion and blood platelet aggregation. There is not a precise structure-activity relationship in the prostaglandin family as much cross-activity is evident.

A great number of studies have been undertaken to enhance, extend and otherwise modify the activity of naturally occurring prostanoic acids. The majority of these studies have focused on modification of two areas, the two side chains and substituents attached to the cyclopropane moiety [see, for example, U. Axen et al, Synthesis Vol. 1, John Whilely and Sons Inc., New York, N.Y. 1973 and P. H. Bently, Chem. Soc. Reviews, 2, 29 (1973)].

Of special interest to this invention is that group of prostaglandins which are labile in most standard pharmaceutical compositions, particularly PGE compounds and PGE-type compounds. In many instances the cyclopentane ring substituents substantially affect the prostaglandin's level of activity. Compounds which loose an oxygen from either C-9 or C-11 on the cyclopentane ring or which have these positions altered show altered levels of activity. For instance $PGE_2\alpha$, which has a carbonyl group at C-9 and an hydroxyl group at C-11 stimulates smooth muscle tissue but loss of the C-11 hydroxyl group to give a double bond in the cyclopentane ring, the PGA or PGB forms, show little or no such activity. This conversion is chemically facile because of the presence of the carbonyl group at C-9 in the PGE and PGE-type compounds which makes the hydroxyl group at C-11 labile to either base or acid dehydroxylation. The product of this dehydroxylation is a double bond conjugated with the carbonyl group of C-9, a stable chemical entity. Under acid conditions PGE-type compounds convert readily to the PGA form. Basic conditions cause PGE-type compounds to dehydroxylate and rearrange to the PGB form. In the case of $PGE_2$ type compounds this latter form is particularly stable because the C-9 carbonyl is now conjugated with the C-8/C-12 and C-13/C-14 double bonds. Similar degradation patterns have been observed in most compounds which have PGE-type cyclopentane ring substituents.

Initial efforts at providing easily dispensible dose formulations of prostaglandins, particularly for PGE-type compounds, met with difficulty. Aqueous PGE solutions were found to undergo rapid loss of activity when stored at temperatures above 0° C. at any pH, but particularly under alkaline conditions. Hydrous solutions adjusted to pH 5–7 were found to be most stable but loss of activity was still so rapid, drug concentrations after several months were very uncertain. Even in neutral or neat solutions there was found gradual degradation. Similar rapid degradation under these conditions have been observed in most compounds which have PGE-type cyclopentane ring substituents.

Various attempts have been made to formulate stable solutions of PGE-type compounds. Stabilization of these compounds has been observed in some solutions and in solid form at −20° C. or lower. More practical and usable alternative methods for stabilizing these prostaglandins have been developed and are described, for example, in U.S. Pat. Nos. 3,749,800; 3,826,823; 3,829,579; 3,851,052; 3,833,725; and 4,221,793. These patents teach the use of such solvents as lower molecular weight alcohols, polyalkylene glycols, dialkylated polyalkylene glycols, triacetin, dimethylacetamide and triethylcitrate. All these disclosure contain the limitation that the solvent and the resulting drug solution must be anhydrous, i.e. contain less than 0.5% water, in order to achieve stable formulations. The dialkylated polyalkylene glycols are excepted from this particular limitation, but prefered formulations using these solvents contain less than 0.5% water.

It has now been found that prostaglandins in general and specifically PGE and PGE-type prostaglandin compounds can be prepared into stable pharmaceutical solution by dissolving them in carbonate diesters. It has also been discovered that the presence of water in such a solution will not significantly affect drug stability even when water is present in an amount up to the solubility limit of water in the chosen carbonate diester. Prostaglandins stablized by such solvents are particularly adaptable for oral administration of therapeutic doses of prostaglandins.

SUMMARY

One aspect of this invention is concerned with novel stable pharmaceutical compositions comprising PGE-type prostaglandins dissolved in carbonate diester solvents which may contain water in an amount up to the solubility limit of the diester solvent. A further aspect is a method of stablizing PGE-type prostaglandins in solution which method consists of dissolving such compounds in a carbonate diester solvent which may contain water up to the solubility limit of the particular solvent. In a third aspect this invention discloses a process for treating a prostaglandin-responsive condition by orally administering a therepeutically effective dose of a PGE or PGE-type compound dissolved in a carbonate diester solvent which may contain water in an amount up to the solubility limit of the diester.

The broadest embodiment of this invention involves dissolving a prostaglandin-like compound, particularly a PGE or PGE-type compound, in a carbonate diester which may contain water in an amount up to the solubility limit of the particular diester. Combinations of these solvents will serve equally well to stabilize the mentioned compounds. Compound concentrations can range from 0.001 to 100 mg/ml of solvent. These solutions are adaptable to use for oral administration when encapsulated with a water dispersible material such as gelatin.

DESCRIPTION OF THE INVENTION

One of the novel aspects of this invention is the use of a certain group of organic solvents for formulating prostaglandins which use has not been previously disclosed. This group of solvents is herein termed "carbonate diesters". This phrase is intended to cover those solvents which can be said to be the condensation product of carbonic acid and two moles of alcohol wherein each acid function of carbonic acid has been converted to an ester by some means. Such diesters may be linear or cyclic, depending on whether the alcohol moiety is a simple alcohol or a polyhydric alcohol. These linear and cylic compounds can be illustrated by Formulas II and III which are as follows:

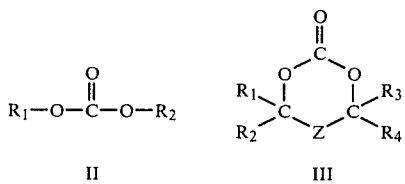

II    III

In Formula II, $R_1$ and $R_2$ are the same or different and are alkyl radicals of 1 to 10 carbon atoms. In Formula III $R_1$ to $R_4$ are the same or different and are hydrogen or alkyl radical of from 1 to 5 carbon atoms; and Z is $(CH_2)_n$ or $(R_5\text{-}C\text{-}R_6)_n$ where $R_5$ and $R_6$ are the same or different and are hydrogen, methyl or ethyl, and n is 0, 1, or 2.

The preferred solvents of this invention are the linear diesters wherein $R_1$ and $R_2$ are the same and are methyl, ethyl or isopropyl and those cyclic diesters where n is 0 and $R_1$ to $R_4$ are hydrogen or $R_1$ is methyl and $R_2$ to $R_4$ are hydrogen. The preferred linear diesters are dimethyl carbonate, diethyl carbonate and diisopropyl carbonate. Preferred Cyclic diesters are ethylene carbonate and propylene carbonate.

In the practice of this invention it is most preferred to use diethyl carbonate or propylene carbonate, particularly propylene carbonate. Propylene carbonate is known by various other names, for example, 4-methyl-1,3-dioxolan-2-one, 1-methylethylene carbonate, and 1,2-propanediol carbonate, to give a few of the most commonly used names. Its CAS number is 108-32-7. It has a molecular weight of 102.09, a boiling point of 241.7° C. and a melting point of −55° C. For the purposes of this invention anhydrous propylene carbonate is that propylene carbonate material which contains less than 0.02% water by Karl Fischer titration. Propylene carbonate is readily available from various manufacturers such as Jefferson Chemical Co., Inc.

The linear carbonate diesters, those of Formula II, are widely known and used and are available commercially. Several of the cyclic carbonate diesters, for example where n is 0 and $R_1$ to $R_4$ are hydrogen or where $R_1$ is methyl and $R_2$ to $R_4$ are hydrogen, are also known and generally available commercially. Preparation of other cyclic carbonate diesters can be carried out by base-catalyzed ester exchange with diethyl carbonate and the appropriate diol, see S. Sarel and L. A. Pohoryles, J. Am. Chem Soc., 80, 4596 (1958); by the reaction of phosgene with diols in the presence of antipyrine according to the method of B. J. Ludwig and E. C. Piech, J. Am, Chem. Soc., 73, 5779 (1951); or by heating an alkylene oxide and carbon dioxide in the presence of a catalyst as described in Japanese Pat. No. 7236738-R. While the methods for preparing such compounds are varied and may not consist of a simple condensation process, the form of the compound is the material factor, not the method of preparation; and it is intended that this invention cover all carbonate diesters as illustrated herein without regard to their source, the method by which they are obtained, or their symmetry.

The only limitation being placed on the selection of a solvent from the described group is that the solvent itself have no deleterious or untoward affects on the subject to which it is administered in the course of a particular treatment regime. It should be understood that this limitation is to be based on the solution as prepared for administration and the route by which it is to be administered. For example, certain diesters might not be pharmaceutically acceptable undiluted but will cause no untoward effects when diluted with a large volume of water as in enteral or intravenous administration or when diluted into a lactose or suppository base for intravaginal or rectal administration. For example, gelatin capsules containing a PGE or PGE-type compound dissolved in a carbonate diester, particularly diethyl carbonate or propylene carbonate, may be administered orally with no resultant adverse pharmacodynamic affects on the subject.

As noted above, while the novelty of this invention lies first in the use of carbonate diesters as solvents for preparing stable solutions of prostaglandins, a second, and equally important discovery, is the fact that water may be present in these solvents in an amount up to the solubility limit of water in a particular diester without significant affect on prostaglandin stability in that solution.

It is normally preferred to prepare and maintain an anhydrous composition where PGE or PGE-type prostaglandin compounds are concerned because of their expected susceptability to degradation in the presence of water, particularly cyclopentane ring dehydroxylation. However, most organic solvents in which prostaglandin acids and even esters are soluble, and which are pharmaceutically acceptable, usually contain a trace amount of water, in the range of up to 0.2% and sometimes as high as 0.5%. Further, initially anhydrous solvents may take up water during the formulation stage or during storage. For example, a water miscible solvent fill of soft gelatin capsules can retain up to 5% water by weight depending upon the nature of the fill material. This is because of the nature of the encapsulation process wherein the prepared gelatin shell mix usually contains up to 30% water at the time the drug containing solution is filled into the encapsulating gelatin. The final capsule form is achieved by drying the prepared capsule at an elevated temperature to remove excess water. During the drying process the encapsulated solution can absorb water from the gelatin and retain all or part of that water in spite of the drying process. Thus, while the prostaglandin solution may be initially prepared in an anhydrous form, after soft gelatin capsules have been prepared therefrom several percent of water may be retained by the encapsulated solution even after extended capsule drying. For example, encapsulated propylene carbonate typically retains about 1% water at ambient temperature and about 2% at 37° C. at 80% relative humidity. The solvents described in the above mentioned patents all specify that water is to be excluded or limited to an amount less than 0.2% in order to obtain a stable prostaglandin solution, a requirement which may be difficult when the above described soft gelatin capsule formulation is prepared.

The solvents of this invention are not faced with the limitations on the amount of water which may be present in a particular solution because it has been found that water may be present in these solvents without significant effect on PGE or PGE-type compound stability. While it may be considered desirable to prepare anhydrous carbonate diester/PGE and PGE-type compounds solutions because of the widely reported stability problems with these compounds in the presence of any protic solvent, anhydrous composition using these solvents are not required or necessarily needed. Anhydrous propylene carbonate solutions of PGE-type compounds have shown no loss of parent drug when stored for 80 days at room temperature. Solutions of PGE-type compounds in a 10% water/propylene carbonate solvent at 45° C. for 28 days have shown less than 1% degradation within the limits of experimental error.

The amount of water which may be present in these solutions is limited only by the solubility of water in a particular diester or diester mixture. Mixtures of water and carbonate diesters may or may not be miscible depending on the solvent characteristics of the diester, temperature, and the ratios in which they are present. Small quantities of water are completely miscible with many of the lower alkyl substituted linear and cyclic diesters such as the preferred solvents set out above. The exact percentage of water which is miscible in a particular diester varies from one to another. It is also a function of temperature. For instance, the solubility of water in propylene carbonate at 20° C. is 8.3%. At 45° C. it is approximately 15%. Similarly, other diesters may have dissolved in them various maximum amounts of water depending on the hydrophilicity of the solvent and temperature. Such a water-diester solvent, it has been found, will not effect significant degradation to PGE and PGE-type compounds dissolved therein, even when water is present in an amount up to its solubility limit in that particular diester or diester mixture.

The solvents of this invention may be used to stabilize all types of prostaglandin compounds but has the greatest utility for PGE compounds and PGE-type compounds. The phrase "PGE compounds" refers to those naturally occuring compounds which are derivatives of prostanoic acid and which have a C-9 carbonyl substituent and C-11 and C-15 hydroxyl substituents. These compounds have varying degrees of unsaturation as discussed above and all are intended to be included within the scope of the phrase "PGE compounds". There is intended to be included in this definition $PGE_1$, $PGE_2$, $PGE_3$ and dihydro-$PGE_1$ compounds. Esters of these compounds have been synthetically prepared, see for example U.S. Pat. Nos. 3,069,332 and 3,598,858.

There also have been prepared many compounds which retain the C-9 carbonyl and C-11 hydroxy cyclopentane ring structural features but wherein the side chains have been modified; and which cause at least part of the biological response caused by PGE compounds. These compounds are intended to be included within the scope of this invention and are covered herein by the phrase "PGE-type compounds". Modified compounds differ from PGE compounds in one or more structural aspects, for example, in having one or more substituents, for example, alkyl, fluoro, phenyl, or cycloalkyl, on one or both side chains; in having fewer or more methylene groups in one or both side chains; in having a hetero atom, for example, oxygen in place of a side-chain methylene group; in having cis rather than a trans or a trans rather than a cis configuration for a side-chain carbon-carbon double bond; in having allenic double bonds in one side chain; or in any combination of those structural aspects. As examples of art which discloses such PGE-type compounds and others, see. U.S. Pat. Nos. 3,639,463; 3,759,978; 3,767,695; 3,781,325; 3,804,889; 3,812,179; 3,813,433; 3,833,640; 3,835,180; 3,842,118; 3,847,966; 3,849,487; 3,855,270; 3,864,387; and 4,178,457. See also German Offenlegungschrift Nos. 1,937,675; 1,937,921; 2,011,969; 2,036,471; 2,118,686; 2,121,980; 2,144,048; 2,150,361; 2,154,309; 2,165,184; 2,209,990; 2,217,044; 2,221,443; 2,317,019; 2,320,552; 2,322,673; 2,332,400; 2,345,685; 2,423,155 and 2,423,156. See also French Pat. No. 2,119,855, Belgian Pat. Nos. 779,898 and 782,822.

Also, for the purposes of this invention, it is intended to include racemic mixtures as well as resolved enantiomers of both PGE and PGE-type compounds.

In both instances it should be understood that not only the carboxylic acids are to be included but also esters of said compounds. Those esters wherein the esterifying radial is alkyl of one to 12 carbon atoms, inclusive, cycloalkyl of 3 to 10 carbon atoms, aralkyl of 7 to 12 carbon atoms, phenyl, and phenyl substituted with 1, 2 or 3 chloro or alkyl of 1 to 4 carbon atoms are typical. Alkyl eaters of 1 to 4 carbon atoms are particularly useful, especially methyl and ethyl esters.

Pharmaceutically acceptable salts of both compound groups are also to be included. These salts may be prepared from pharmaceutically acceptable non-toxic bases, including inorganic and organic bases. Salts derived from inorganic bases include, preferably, ammonium, potassium, sodium, calcium and magnesium salts.

Preferred organic bases are isopropylamine, diethylamine, ethanolamine, peperidine, tromethamine, choline and caffine.

Of particular interest are stable compositions of PGE-type compounds wherein the prostaglandins are 16-phenoxy and 16-substituted phenoxy prostaglandin E analogs represented by the following formula:

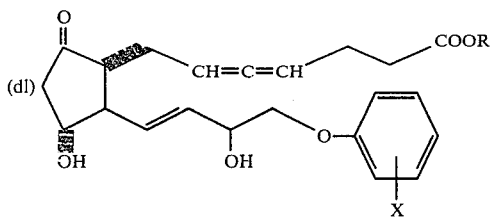

IV wherein R is hydrogen, a lower alkyl group of 1 to 4 carbon atoms, or the pharmaceutically acceptable, non-toxic salts of compounds in which R is hydrogen; and X is hydrogen, o-, m- or p-halo (fluoro, chloro or bromo), o, m- or p-methyl or o-, m- or p-methoxy.

The lines shown in the above formula and in the formulas below as " ▄ " indicate that the substituents are in α configuration, i.e., below the plane of the cyclopentane ring.

The double bond at C-13 has the same configuration as in natural prostaglandins of the PGE and PGF series, that is the trans configuration.

These novel compounds possess asymmetric centers and thus can be produced as racemic "(dl)" mixtures or as individual 8R-antimers. The racemic mixtures can be resolved if desired at appropriate stages by methods known to those skilled in the art, to obtain the respective individual antimers.

These particular compounds exhibit prostaglandin-like biological activity and thus are useful in the treatment of mammals where the use of prostaglandins is indicated. These compounds are useful for the control of asthmatic attack because they are bronchodilators and they also exhibit antiallergic properties by inhibition of mediator release. In addition, they are also useful for treating mammals for bronchial spasm or wherever bronchodilator compounds also exhibit vasodilator properties and are useful in controlling palpitating hypertension in mammals. They further exhibit central nervous system depressant activity in mammals, and are useful as sedatives. Most particularly, compounds of this formula have been found to be potent inhibitors of gastric secretion and ulcer induction and thus are extremely useful in the treatment and prevention of gastric and duodenal ulcers. The compounds are the subject of U.S. Pat. No. 4,178,457 which is incorporated herein by reference.

In the practice of this invention, prostaglandin concentrations may range from 0.001 to 100 mg/ml of chosen solvent. While the particular concentration for a given prostaglandin will depend on its inherent level of activity and the therepeutic dose to be adminstered at a particular time and by a particular route, a preferred concentration range will be between 0.01 mg/ml and 20 mg/ml. The most preferred concentration range is about 0.01 mg/ml to 5.0 mg/ml, particularly for the compounds represented by Formula IV.

If a dosage form suitable for oral administration is desired, the prostaglandin solvent composition may be encapsulated by art recognized methods in a pharmaceutically acceptable water dispersable material suitable for oral administration, for example, gelatin. Herein, soft gelatin capsules are the preferred dose form for oral administration.

SPECIFIC EMBODIMENTS OF THE INVENTION

In the general case, the compositions of this invention are prepared by adding the prostaglandin to the carbonate diester solvent at the desired concentration and stirring the admixture at room temperature until a homogenous solution is obtained. Such procedure provides an effective method for stabilizing PGE and PGE-type compound compositions. This procedure also acts as the first step in the process for dispensing for oral administration a PGE or PGE-type compound, the subsequent steps being to encapsulate the solution in a pharmaceutically acceptable water dispersable material suitable for oral administration and administering said vehicle in such a manner so as to administer a therapeutic dose to the subject.

The following examples set out general descriptions of means for practicing the invention as describes herein.

EXAMPLE 1

To 10 ml of anhydrous propylene carbonate at 25° C. is added from about 0.01 to 10 mg of (dl)-9-keto-11α,1-5α-dihydroxy-16-phenoxy-17,18,19,20-tetranorprosta-4,5,13-trans-trienoic acid methyl ester. The mixture is stirred with a blade type stirrer for 15 minutes until an homogenous solution is obtained.

EXAMPLE 2

Following the procedure of Example 1, a solution of the same prostaglandin at the same concentrations was dissolved in propylene carbonate containing 5% water by weight.

EXAMPLE 3

The methyl ester of the trienoic acid methyl ester set out in Example 1 was prepared as a stable composition by adding 0.01 to 10 mg of the compound to 10 ml of propylene carbonate containing 8.3% water by weight and stirring with a blade-type mixer until a homogenous solution was obtained.

EXAMPLE 4

The products of Examples 1, 2 or 3 may be utilized in an oral dosage form by adding the homogenous propylene carbonate/trienoic acid methyl ester mixture to a soft-shelled gelatin capsule prepared by art recognized methods. The above mentioned compounds, in a variety of concentrations, are then typically administered for the reduction of gastric secretion and the prevention or healing of peptic ulcers in humans, or for other prostaglandin therapeutic uses.

EXAMPLE 5

Table I sets out study results wherein an E-type prostaglandin, (dl)-9-keto-11α,15α-dihydroxy-16-phenoxy-17,18,19,20-tetranorprosta-4,5,13-trans-trienoic acid methyl ester, at a concentration of 0.5 mg/ml, was dissolved in 0.1% water-propylene carbonate and stored at several elevated temperatures for up to 90 days. The same amount of trienoic acid methyl ester was dissolved in propylene carbonate containing 5.0% and 10.0% water and these solutions stored at 45° C. for 60 days.

The results demonstrate good drug stability in all of these solutions. These results are in comparison to a $T_{90}$ of 8 days at 25° C. in a aqueous solution at pH=3, the most stable pH for this compound.

The aforementioned examples are merely illustrative of the intended invention and are in no way expressly limiting of the invention. The invention is limited solely by the claims.

TABLE I

STABILITY OF AN E-TYPE+ PROSTAGLANDIN IN PROPYLENE CARBONATE (0.5 mg/ml)

| | % DRUG REMAINING | | | | | |
|---|---|---|---|---|---|---|
| | 0.1% H₂O | | | | 5% H₂O | 10% H₂O |
| DAYS | 40° C. | 50° C. | 60° C. | 80° C. | 45° C. | 45° C. |
| 0 | 100 | 100 | 100 | 100 | 100 | 100 |
| 7 | — | — | — | 98.3 | 104 | 103 |
| 14 | — | — | 100 | 97.6 | 103 | 99.0 |
| 21 | — | 99.3 | — | 97.4 | — | — |
| 28 | — | — | 96.7 | 96.2 | 98.6 | 102 |
| 60 | 99.6 | 97.9 | 94.8 | 92.5 | 97.3 | 88.6 |
| 90 | — | — | 92.8 | 90.4 | — | — |

+(dl)-9-keto-11α,15α-dihydroxy-16-phenoxy-17,18,19,20-tetranorprosta-4,5,13-trans-trienoic acid methyl ester

What is claimed is:

1. A stable pharmaceutical composition comprising a PGE or PGE-type compound dissolved in a cyclic carbonate diester solvent which may contain water in an amount up to the solubility limit of water for the diester solvent encapsulated in a soft shelled gelatin capsule.

2. A stable composition according to claim 1 wherein said compound is present in an amount between 0.001 mg to 100 mg per ml of solvent.

3. A stable composition according to claim 2 wherein said compound is selected from those represented by the formula:

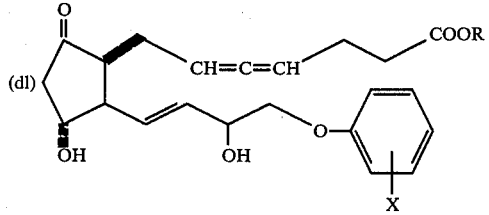

wherein:
R is hydrogen, a lower alkyl group of 1 to 4 carbon atoms, or the pharmaceutically acceptable, non-toxic salts of compounds in which R is hydrogen; and X is hydrogen, o-, m- or p-halo, o, m- or p-methyl or o-, m- or p-methoxy.

4. A stable composition according to claim 3 wherein said compound is present in an amount between 0.01 mg to 20 mg per ml and said diester is propylene carbonate.

5. A stable composition according to claim 4 wherein the compound is (dl)-9-keto-11α,15α-dihydroxy-16-phenoxy-17,18,-19,20-tetranorprosta-4,5,13-trans-trienoic acid methyl ester and is present in an amount between 0.01 mg to 5 mg per ml.

6. A method for preparing a stable soft-shelled gelatin capsule composition of PGE or PGE-type compounds which comprises dissolving at least one of said compounds in a cyclic carbonate diester solvent which may contain water in an amount up to the solubility limit of water in the diester solvent and adding the mixture to a soft-shelled gelatin capsule.

7. The method of claim 6 wherein said compound is present in an amount between 0.001 mg to 100 mg per ml solvent.

8. The method of claim 7 wherein said compound is selected from those represented by the formula:

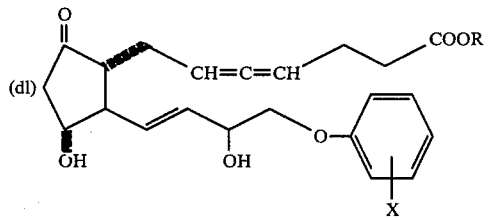

wherein:
R is hydrogen, a lower alkyl group of 1 to 4 carbon atoms, or the pharmaceutically acceptable, non-toxic salts of compounds in which R is hydrogen; and X is hydrogen, o-, m- or p-halo, o, m- or p-methyl or o-, m- or p-methoxy.

9. The method of claim 8 wherein said compound is present in an amount between 0.01 mg to 20 mg per ml; and said diester is propylene carbonate.

10. The method of claim 9 wherein the compound is (dl)-9-keto-11α,15α-dihydroxy-16-phenoxy-17,18,-19,20-tetranorprosta-4,5,13-trans-trienoic acid methyl ester and is present in an amount between 0.01 mg to 5 mg per ml.

* * * * *